United States Patent [19]

DeLuca et al.

[11] 4,411,833
[45] Oct. 25, 1983

[54] METHOD FOR PREPARING 26,26,26,27,27,27-HEXAFLUORO-1α,25-DIHYDROXYCHOLESTEROL

[75] Inventors: Hector F. DeLuca; Yoko Tanaka, both of Madison, Wis.; Nobuo Ikekawa, Musashinoshi; Yoshiro Kobayashi, Tokyo, both of Japan

[73] Assignee: Wisconsin Alumni Research Foundation, Madison, Wis.

[21] Appl. No.: 382,055

[22] Filed: May 26, 1982

[51] Int. Cl.$^3$ .............................................. C07J 17/00
[52] U.S. Cl. ........................ 260/239.55 R; 260/397.2; 260/397.5; 260/397.1
[58] Field of Search .............. 260/397.1, 397.2, 239.55

[56] References Cited

U.S. PATENT DOCUMENTS 4,305,881 12/1981 Furst et al. ........................ 260/397.2
4,358,406 11/1982 DeLuca et al. .................. 260/397.2

Primary Examiner—Elbert L. Roberts
Attorney, Agent, or Firm—Howard W. Bremer

[57] ABSTRACT

This invention provides a new method for preparing 26,26,26,27,27,27-hexafluoro-1,25-dihydroxycholesterol.

The method permits the use of cholenic acid or an ester of cholenic acid as the starting material and the preparation of a compound which can be readily converted into a highly active derivative of vitamin D, 26,26,26,27,27,27-hexafluoro-1α,25-dihydroxycholecalciferol.

3 Claims, No Drawings

METHOD FOR PREPARING 26,26,26,27,27,27-HEXAFLUORO-1α,25-DIHYDROXYCHOLESTEROL

The invention described herein was made in the course of work under a grant or award from the Department of Health, and Human Services

DESCRIPTION

Technical Field

This invention relates to the preparation of a compound which can be readily converted to a compound having vitamin D-like activity.

More specifically, this invention relates to a method for preparing 26,26,26,27,27,27-hexafluoro-1α,25-dihydroxycholesterol.

Vitamin $D_3$ is a well-known agent for the control of calcium and phosphorous homeostasis. In the normal animal or human this compound is known to stimulate intestinal calcium transport.

It is also now well known that to be effective, vitamin $D_3$ must be converted to its hydroxylated forms. For example, the vitamin is first hydroxylated in the liver to form 25-hydroxy vitamin $D_3$ and is further hydroxylated in the kidney to produce 1α,25-dihydroxy vitamin $D_3$ or 24,25-dihydroxy vitamin $D_3$. The 1α-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

Background Art

Since the discovery of biologically active metabolites of vitamin D there has been much interest in the preparation of structural analogs of these metabolites, because such compounds may represent useful therapeutic agents for the treatment of diseases resulting from calcium metabolism disorders. A variety of vitamin D-like compounds have been synthesized. See, for example, U.S. Pat. Nos. 3,741,996 directed to 1α-hydroxycholecalciferol; 3,907,843 directed to 1α-hydroxyergocalciferol; 3,786,062 directed to 22-dehydro-25-hydroxycholecalciferol; 3,906,014 directed to 3-deoxy-1α-hydroxycholecalciferol; and 4,069,321 directed to the preparation of various side chain-fluorinated vitamin $D_3$ derivatives and side chain-fluorinated vitamin $D_3$ derivatives and side chain-fluorinated dihydrotachysterol analogs.

A fluoro derivative of the accepted hormonal form of the vitamin, 1,25-dihydroxycholecalciferol, (1,25-$(OH)_2D_3$), of particular interest is 24,24-difluoro-1,25-$(OH)_2D_3$ because it is characterized by at least as great if not greater activity than 1,25-$(OH)_2D_3$. (See U.S. Pat. No. 4,201,881.)

Also of interest is the 26,26,26,27,27,27-hexafluoro derivative of 25-hydroxycholecalciferol (see U.S. Pat. No. 4,248,791) and the 26,26,26,27,27,27-hexafluoro derivative of 1α,25-dihydroxycholecalciferol (application for U.S. patent Ser. No. 286,790, filed July 27, 1981 now U.S. Pat No. 4,358,406) which is characterized by substantially greater vitamin D-like activity than the hormonal form of the vitamin, 1,25-dihydroxycholecalciferol, in its ability to stimulate calcium transport in the intestine, to mobilize calcium from bone and in its antirachitic activity according to the rat line test.

Disclosure of Invention

A new method for preparing 26,26,26,27,27,27-hexafluoro-1α,25-dihydroxycholesterol has now been devised. This compound lends itself to easy conversion to the highly active 26,26,26,27,27,27-hexafluoro-1α,25-dihydroxycholecalciferol.

In this method, which is illustrated in the following schematic, commercially available cholenic acid was converted to the ester (1), which was oxidized with dichlorodicyanobenzoquinone (DDQ) to give the trienone (2). Treatment of the trienone (2) with alkaline hydrogen peroxide afforded the 1,2-epoxide (3), which was reduced with lithium metal and ammonium chloride in liquid ammonia-tetrahydrofuran yielding the triol (4) (65%) yield. After tritylation followed by acetylation and hydrolysis, 1,3-diacetate (5) was obtained in 72% yield. The 24-ol (5) was converted to the bromide via 24-tosylate, and then to the phenylsulfone (7). After conversion to the 1,3-ditriethylsilyl derivative (9), the sulfone was treated with hexafluoroacetone to give the hexafluoro-phenyl-sulfone (10). Hydrolysis with HCl to give the corresponding triol and then sodium amalgam reduction afforded the hexafluoro-1,25-dihydroxycholesterol (11) in 72% yield.

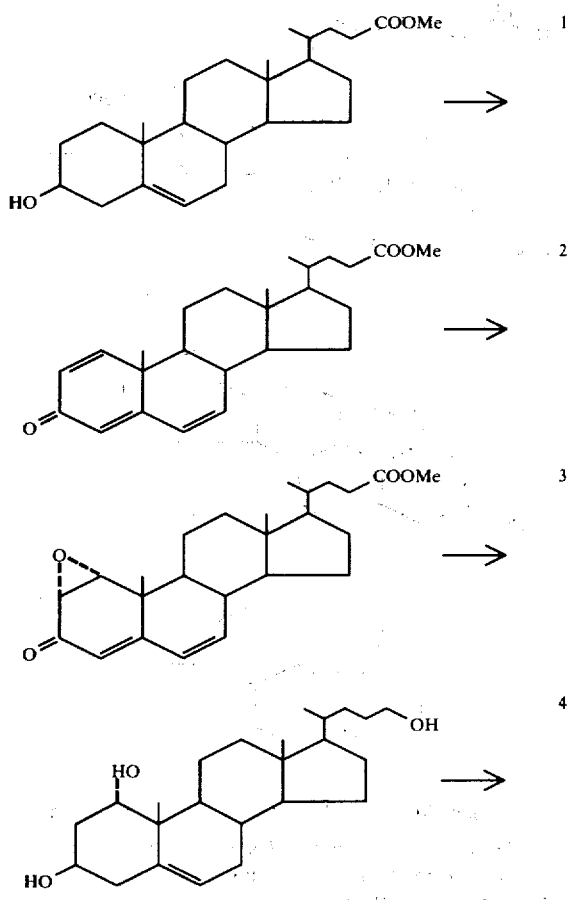

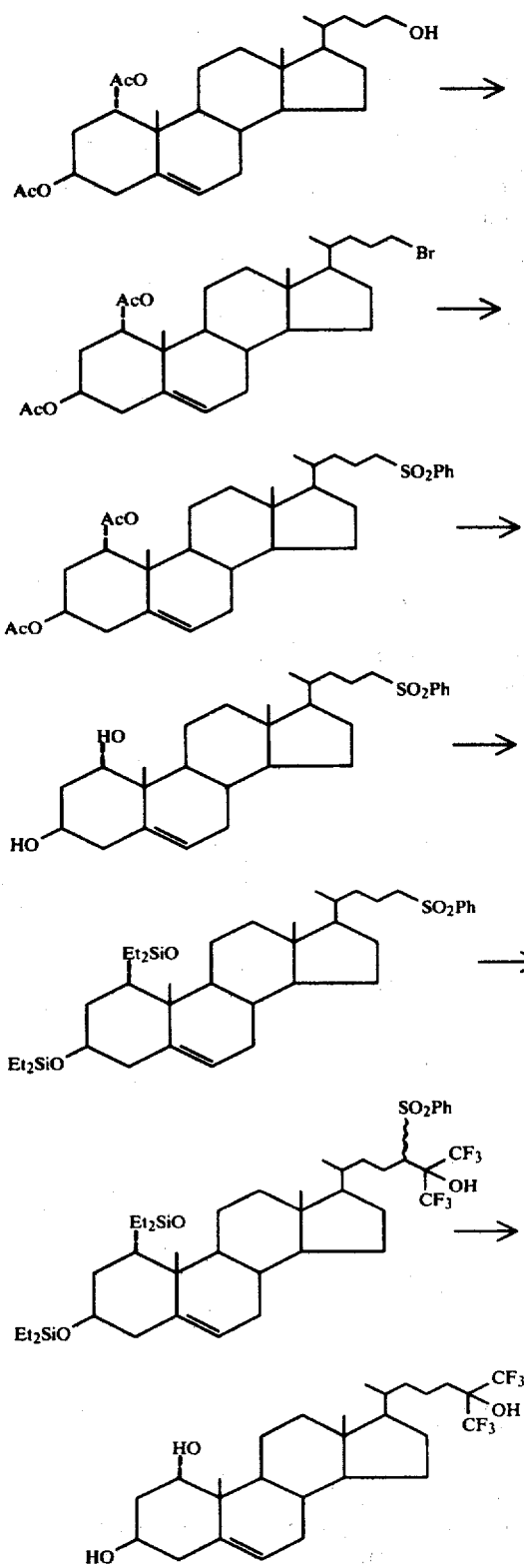

Best Mode for Carrying Out the Invention

The following detailed description of the process of the invention should be considered in conjunction with the foregoing schematic.

The conversion of cholenic acid to the ester (1) can be readily accomplished by known methods as will be evident to those skilled in the art.

25,26,27-Trinorcholesta-1,4,6-trien-3-on-24-oic acid methyl ester (2)

A solution of the ester (1) (110 g, 0.28 mol) and dichlorodicyanobenzoquinone (212 g, 3.3 eq) in dioxane (850 ml) was refluxed for 14 hr under nitrogen. After being cooled, the resulting precipitate was filtered off and washed with several portions of $CH_2Cl_2$. The filtrate was evaporated to dryness and the residue was chromatographed on alumina (2 kg). Elution with benzene-AcOEt (50:1) gave the trienone (2) (60 g, 55%). mp 134°–136° (from methanol); $[\alpha]_D^{30} = -42.5°$ (C=1, $CHCl_3$); UV (EtOH),λmax 299 (ε13,000), 258 (ε9,200); 223 nm (ε12,000); IR ($CHCl_3$), 1730, 1655 cm$^{-1}$; $^1$H-NMR, δ0.80 (3H, s, 18-$H_3$), 0.93 (3H, d, J=6 Hz, 21-$H_3$), 1.2 (3H, s, 19-$H_3$), 3.68 (3H, s, —$CO_2Me$), 5.90–6.30 (4H, m, 2-,4-,6- and 7-H), 7.05 (1H, d, J=10 Hz, 1-H), (Found; M+, 382.2494, $CH_{25}H_{34}O_3$ requires M, 382.2505).

25,26,27-Trinor-1α,2β-epoxy cholesta-4,6-dien-3-on-24oic acid methyl ester (3)

A solution of the trienone (2) (30 g, 0.0785 mol) in methanol (550 ml) was added to a mixture of 5% NaOH-MeOH (15 ml), and 30% $H_2O_2$ (42 ml). The reaction mixture was allowed to stand at room temperature for 18 hr, and was extracted with AcOEt and the extract was washed with brine, dried over $Na_2SO_4$ and evaporated. Chromatography on silica gel (400 g), eluting with benzene-AcOEt (100:1), gave the epoxide (3) (24.8 g, 80%). mp 166°–168° (from methanol), $[\alpha]_D^{27} = +187.3°$ (C=1, $CHCl_3$), UV (EtOH),εmax 290 nm (ε22,000); IR ($CHCl_3$), 1730, 1660 cm$^{-1}$; $^1$H-NMR, 0.78 (3H, s, 18-H), 0.95 (3H, d, J=6 Hz, 21-$H_3$) 1.18 (3H, s, 19-$H_3$), 3.42 (1H, dd, J-4 and 1.5 Hz, 1-H), 3.58 (1H, d, J=4 Hz; 2β-H), 3.67 (3H, s, —$CO_2Me$); 5.61 (1H, d, J=1.5 Hz, 4-H), 6.04 (2H, brs, 6- and 7-H), (Found; C 75.27, H, 8.61, $CH_{25}H_{34}O_4$ requires C, 75.34; H, 8.60).

25,26,27-Trinorcholest-5-ene-1α,3β,24-triol(4)

A four-necked flask was fitted with a sealed mechanical stirrer, a dropping funnel, a cold-finger fill with dry ice and inlet connected to an anhydrous ammonia source. Nitrogen was swept through the system and then anhydrous ammonia (1000 ml) was trapped in the flask with cooling bath (dry ice-methanol). Lithium wire (30.5 g) was cut into short pieces and added during 30 min. After stirring for 1 hr, the epoxide (3) (21.7 g, 0.054 mol) in dry THF (1000 ml) was added dropwise during 1.5 hr. Then, anhydrous $NH_4Cl$ (350 g) was added during 2 hr, the mixture turned white and pasty. The cooling bath was removed and most of ammonia was removed in a stream of nitrogen. Water was carefully added and the mixture was extracted with AcOEt. Extract was washed with dil HCl, sat'd $NaHCO_3$ and brine, dried over $Na_2SO_4$ and evaporated to dryness. Chromatography on silica gel (350 g), eluting with benzeneacetone (3:1), gave the product (13.9 g, 65%). m.p. 210–211 (from methanol-acetone); $[\alpha]_D^{26} = -17.4°$ (C,1, methanol); IR (KBR) 3400 cm$^{-1}$; $^1$H-NMR (py-$d_5$ $CDCl_3$, 1:1) δ0.67 (3H, s, 18-$H_3$), 1.02 (3H, s, 21-$H_3$), 3.69 (2H, m, 24-$H_2$), 3.95 (1H, m, 1α-H), 4.40 (1H, m, 3-H) 5.50 (1H, m, 6-m), (Found; M+ 376.2956, $CH_{24}H_{30}O_3$ requires M, 376,2974).

25,26,27-Trinorcholest-5-ene-1α,3β,24-triol 1,3-diacetate (5)

A solution of the triol (4) (1.0 g) and trityl chloride (2.2 g) in pyridine (10 ml) was stirred at room temperature overnight. To this reaction mixture, acetic anhydride (2 ml) and a catalytic amount of dimethylaminopyridine were added, and the mixture was stirred at 40° C. for 4 hr. The usual work-up gave 1α,3β-Diacetoxychol-5-en-24-yl tritylate. (By the use of alternative acylating reagents, i.e. the appropriate acid anhydrides or acyl chlorides (e.g. benzoyl chloride, propionic anhydride, etc.) in accordance with techniques well known in the art, 1,3-diacyl compounds corresponding to (5) but where the acyl group is, for example, benzoyl or propionyl, can be readily obtained.) The crude trityl ether was treated with aqueous dioxane (50 ml) containing a catalytic amount of p-TsoH at 90°–100° C. for 3 hr. After usual work-up, with AcOEt for extraction, the crude produce was chromatographed on silica gel (50 g). The fraction eluted with benzene-AcOEt (10:1) gave the desired diacetate (5) (880 mg) as an amorphous powder; $[\alpha]_D^{26} - 16.4°$ (C 1.05); NMR, δ0.68 (3H, S, 13-Me), 0.92 (3H, d, J=6 Hz, 20-Me), 1.10(3H, s, 10-Me), 2.02, 2.06 (6H, each s, acetyl) 3.59 (2H, t, J=6 Hz, 24-H$_2$), 4.90 (1H, m, 3α-H), 5.04 (1H, m, 1β-H), 5.51 (1H, m 6H); λmax (CHCl$_3$) 3450, 1730, and 1250 cm$^{-1}$; (Found: M$^+$ −2AcOH, 340.2765, C$_{24}$H$_{36}$O requires M, 340.2765).

Treatment of the 1,3-diacetate (5) with acetic anhydride/pyridine provides the corresponding 1,3,25-triacetoxy derivative. Other C-24-acylates (e.g. propionates, benzoates, etc.) can be readily obtained by treatment of (5) with the appropriate acid anhydride on acid chloride under standard conditions as is well known in the art.

25,26,27-Trinorcholest-24-bromo-5-ene-1α,3β-diol diacetate (6)

To a solution of (5) (177 mg) in pyridine (3 ml), tosyl-chloride (96.8 mg) was added at 0° C., and the mixture was stirred at 0° C. overnight. Several pieces of ice were added and the whole was stirred for 1 hr. The usual work-up, with AcOEt for extraction, gave a colorless oil of the tosylate (149 mg). To a solution of the tosylate (149 mg) in DMF (5 ml), LiBr (42.2 mg) was added, and the mixture was refluxed under argon atmosphere for 2 hr. The reaction mixture was cooled, water and AcOEt were added, and the organic phase was washed consecutively with 2N-HCl, dilute NaHCO$_3$, and saturated NaCl and dried (MgSO$_4$). The residue obtained upon evaporation of the solvent was purified by column chromatography on silica gel (4 g). Eluting with benzene gave the bromide (6) (107 mg), mp 127°–129° (from hexane); $[\alpha]_D^{26} - 16.9°$ (C 1.00).

25,26,27-Trinor-1α,3β-diacetoxycholest-5-ene-24-yl phenylsulfone (7)

To a solution of the bromide (6) (164 mg) in DMF (8 ml) PhSO$_2$Na (260 mg) was added, and the suspension was stirred at 70°–80° C. for 4 hr. The reaction mixture was cooled, and extracted with ether. The organic phase was washed with 2N-HCl, dilute-NaHCO$_3$, and brine, and dried over MgSO$_4$. The residue obtained upon evaporation of the solvent was chromatographed on silica gel (20 ). Eluting with benzene gave the sulfone (7) (169 mg) as an amorphous powder; $[\alpha]_D^{28} - 16.9°$ (C 0.66); NMR, δ0.64 (3H, s, 13-ME), 0.86 (3H, d, J=6 Hz, 20-Me), 1.08 (3H, s, 10-Me), 2.02, 2.05 (6H, each s, acetyl), 3.04 (2H, t, J=7 Hz, 24-H$_2$), 4.91 (1H, m, 3α-H), 5.04 (1H, m, 1α-H), 5.50 (1H, m, 6H), 7.50-(5H, Ar-).

25,26,27-Trinorcholest-1α,3β-diol-5-enyl phenylsulfone (8)

A solution of the diacetate (7) (42.8 mg) in 5% KOH-MeOH (3 ml ) and THF (2ml) was stirred at r..t. for 18 hr. After the usual work-up, the product was purified by column chromatography on silica gel (8 gm). Eluting with hexaneAcOEt (1:1) gave the desired diol (8) (31.2 mg), mp 110°–111° C. (CH$_2$Cl$_2$-hexane).

25,26,27-Trinor-1α,3β-bistriethylsiloxycholesteryl phenyl sulfone (9)

After reaction of 75 mg (150 mol) of (8) with triethylsilyl chloride (0.3 ml) and triethylamine (0.5 ml) in pyridine (3 ml) at room temperature for 15 hr, the reaction mixture was poured into ice-water and extracted with ether. The organic layer was successively washed with 0.5 N-HCl, brine and then dried over MgSO$_4$. The extracts were submitted to column chromatography (SiO$_2$) to give 61.8 mg (85 mol, 57%) of (9); oil, MS m/e 728, 596 (M$^+$−HOSiEt$_3$), 567, 464, 301; NMR, δ(CDCl$_3$) 0.44–0.70 (15H, m, C-18 and SiCH$_2$CH$_3$), 3.07 (2H, t, J=7 Hz, C-24), 3.83 (1H, m, C-1), 4.00 (1H, m C-3), 5.50 (1H, m, C-6), 7.50–7.80 (3H, m) 7.95–8.10 (2H, m).

1,25-Dihydroxy-26,26,26,27,27,27-hexafluorocholesteryl 24-phenylsulfone 1,3-ditriethylsilyl ether (10)

To a solution of diisopropylamine (28 1, 200 mol) in THF (2 ml) was added n-BuLi (190 mol) at −78° C. under argon atmosphere and the resulting solution was stirred for 5 min. To this LDA solution was added 9 (58 mg; 80 mol); in THF (3 ml) and the reaction mixture was stirred for 20 min. at 0° C. This was recooled to −78° C. (dry ice-acetone bath) and was treated with an excess amount of hexafluoroacetone gas for 3 min. at the same temperature. The reaction mixture was quenched by addition of NH$_4$Cl solution and extracted with ether. The organic layer was washed with brine, dried over MgSo$_4$ and then purified by silica gel chromatography. The fraction eluted with benzene afforded 53 mg (74%) of the adduct (10) as a stereosiomeric mixture; NMR, δ(CDCl$_3$), 3.53 (1H, m, C-24), 3.81 (1H, m, C-1), 3.98 (1H, m, C-3), 5.47 (1H, m, C-6), 6.80 (1H, broad, 25-OH), 7.67-7.87 (3H, m), 8.00-8.13 (2H, m); $^{19}$F-NMR (CDCl$_3$) δ+7.8 and +1.08 ppm.

1α,25-Dihydroxy-26,26,26,27,27,27-hexafluorocholesterol (11)

A solution of 45 mg of (10) in a mixture of dimethoxyethane (1 ml), MeOH (1 ml) and 1N-NCl (1 ml) was stirred for 1 hr at room temperature. The reaction mixture was diluted with brine and extracted with ethyl acetate. After the organic extracts were concentrated in vacuo, the residue was chromatographed on silica gel (CH$_2$Cl$_2$-AcOEt 2:3 v/v) to give 34.0 mg (100%) of the triol: NMR, δ(CDCl$_3$), 0.60 (s, C-18), 0.77 (d, J=6 Hz, C-21), 1.00 (s, C-19), 1.70 (1-OH and 3-OH), 3.50 (1H, m, C-24), 3.83 (1H, m, C-1), 4.00 (1H, m, C-3), 5.60 (1H, m, C-6), 6.77 (1H, broad, 25-OH), 7.43–7.87 (3H, m), 8.00–8.10 (2H, m); $^{19}$F-NMR (CDCl$_3$), δ+7.7 and +10.8 ppm. (If desired, the 1,3-triol can be acetylated to the 1,3-di-0-acyl or 1,3,25-tri-0-acyl, e.g. acetyl, benzoyl, products by means of standard acrylating reagents such as acid anhydrides or acyl chlorides under conditions well known by those skilled in the art.) To a mixture of 31 mg of the triol and 50 mg of Na₂HPO₄ in THF (2 ml) and MeOH (2 ml) was added 800 mg of 5%-Na-(Hg) and the whole was stirred for 45 min at room temperature. To this was added further 300 mg of 5% Na(Hg) and the reaction mixture was stirred for 1.5 hr at room temperature. The reaction mixture was diluted with brine and extracted with AcOEt. The extracts were chromatographed on silica gel (CH₂Cl₂-AcOEt 1:2) to give 17.6 mg (72%) of the desired hexafluoride (11); mp 201°-202° (from CHCl₃). The spectrum data (NMR, and mass spectrum) of (11) were identical with those of an authentic sample.

The 26,26,26,27,27,27-hexafluoro-1α,25-hydroxycholesterol can be converted to 26,26,26,27,27,27-hexafluoro-1α,25-dihydroxycholecalciferol in accordance with the process set forth in application for U.S. patent Ser. No. 286,790, filed July 27, 1981 now U.S. Pat. No. 4,358,406.

What is claimed is:

1. A method for preparing 26,26,26,27,27,27-hexafluoro-1α,25-dihydroxycholesterol which comprises oxidizing an ester of cholenic acid with DDQ to obtain 25,26,27-trinorcholesta-1,4,6-trien-3-on-24-oic acid ester;

treating said trienone with alkaline hydrogen peroxide and recovering 25,26,27-trinor-1α,2β-epoxycholesta-4,6-dien-3-on-24-oic acid ester, reducing said epoxide to obtain 25,26,27-trinorcholest-5-ene-1α,3β,24-triol, subjecting said thiol to tritylation and subsequent acetylation and hydroylsis and recovering 25,26,27-trinorcholest-5-ene-1α,3β,24-triol-1,3-diacetate, converting said diacetate to the corresponding 24-toxylate followed by bromination to obtain 25,26,27-trinorcholest-24-bromo-5-ene-1α,3β-diol diacetate, reacting said 24-bromo-diacetate with phenyl sulfonyl sodium to convert it to the corresponding 24-phenylsulfone and hydrolying said sulfone to obtain 25,26,27-trinorcholest-1α,3β-diol-5-enyl phenylsulfone, converting said 1α,3β-diol-phenylsulfone to 25,26,27-trinor-1α,3β-bistriethyl-siloxycholestenyl phenylsulfone by reaction with triethylsilyl chloride and triethylamine, treating said 1α,3β-ditriethylsilyl derivative with hexafluoro acetone and recovering 1,25-dihydroxy-26,26,26,27,27,27-hexafluoro-cholesteryl-24-phenylsulfone-1,3-ditriethylsilyl ether, hydroylzing said ether, reducing the resulting product with sodium amalgam and recovering 1α,25-dihydroxy-26,26,26,27,27,27-hexafluorocholesterol.

2. 25,26,27-trinor-1α,2β-epoxy-cholesta-4,6-dien-3-on-24 oic acid methyl ester.

3. Compounds having the formula

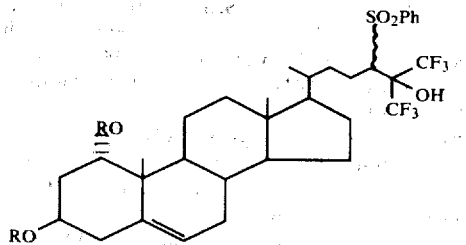

where R is hydrogen, acyl or alkylsilyl.

* * * * *